United States Patent [19]
Granados et al.

[11] Patent Number: 5,955,268
[45] Date of Patent: *Sep. 21, 1999

[54] METHOD AND REAGENT FOR DETECTING MULTIPLE NUCLEIC ACID SEQUENCES IN A TEST SAMPLE

[75] Inventors: Edward N. Granados, Vernon Hills; Stanley R. Bouma, Grayslake; John J. Carrino, Gurnee; Natalie A. Solomon, Buffalo Grove, all of Ill.

[73] Assignee: Abbott Laboratories, Abbott Park, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/639,224

[22] Filed: Apr. 26, 1996

[51] Int. Cl.⁶ .............. C12Q 1/68; C12P 19/34; C12N 9/12; C07H 21/04
[52] U.S. Cl. ............ 435/6; 435/91.2; 435/91.5; 435/91.51; 435/194; 935/6; 935/17; 935/77; 935/78
[58] Field of Search ................. 435/6, 91, 194, 435/91.2, 91.5, 91.51; 536/22.1, 24.3, 24.33; 935/6, 17, 77, 78

[56] References Cited

U.S. PATENT DOCUMENTS

| | | | |
|---|---|---|---|
| 4,876,187 | 10/1989 | Duck et al. | 435/6 |
| 5,011,769 | 4/1991 | Duck et al. | 435/6 |
| 5,210,015 | 5/1993 | Gelfand et al. | 435/6 |
| 5,332,659 | 7/1994 | Kidwell | 435/6 |
| 5,487,972 | 1/1996 | Gelfand et al. | 435/6 |
| 5,538,848 | 7/1996 | Livak et al. | 435/5 |
| 5,670,315 | 9/1997 | Yamamoto et al. | 435/6 |

FOREIGN PATENT DOCUMENTS

| | | | |
|---|---|---|---|
| 8909284 | 10/1989 | WIPO . | |
| WO 90/01564 | 2/1990 | WIPO | C12Q 1/68 |
| WO 95/08642 | 3/1995 | WIPO | C12Q 1/68 |
| 9513399 | 5/1995 | WIPO . | |
| 9615270 | 5/1996 | WIPO . | |

OTHER PUBLICATIONS

Cloney, L., et al., "A Simple Highly Sensitive Nucleic Acid Amplification", *Clinical Chemistry*, 40(4):656 (XP002042545) (1994).

Holland, P. M., et al., "Detection of Specific Polymerase Chain Reaction Product by Utilizing the 5'→3' Exonuclease Activity of *Thermus aquaticus* DNA Polymerase", *Proceedings of the National Academy of Science of USA*, 88:7276–7280 (1991).

*Primary Examiner*—Stephanie Zitomer
*Attorney, Agent, or Firm*—Paul D. Yasger

[57] ABSTRACT

Provided herein are methods for detecting multiple target nucleic acid sequences in a test sample. Also provided is a hybridization platform useful for detecting multiple target sequences in a test sample. The hybridization platform comprises a solid support material having a defined pattern of capture probes immobilized thereon.

11 Claims, 3 Drawing Sheets

```
SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: synthetic DNA (xi) SEQUENCE DESCRIPTION: SEQ ID NO:1:

AGTGGGGGGA CATCAAGCAG CCATGCAAAT                                           30

(2) INFORMATION FOR SEQ ID NO:2:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: synthetic DNA (xi) SEQUENCE DESCRIPTION: SEQ ID NO:2:

TGCTATGTCA CTTCCCCTTG GTTCTCT                                              27

(2) INFORMATION FOR SEQ ID NO:3:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: synthetic DNA (xi) SEQUENCE DESCRIPTION: SEQ ID NO:3:

GAGACCATCA ATGAGGAAGC TGCAGAATGG GAT                                       33

(2) INFORMATION FOR SEQ ID NO: 4:

(i) SEQUENCE CHARACTERISTICS:
          (A) LENGTH: 25
          (B) TYPE:  nucleic acid
          (C) STRANDEDNESS: single
          (D) TOPOLOGY:  linear (ii) MOLECULE TYPE: synthetic DNA (xi) SEQUENCE DESCRIPTION: SEQ ID NO: 4:

TCACCCACAC TGTGCCCATC TACGA                                                25

(2) INFORMATION FOR SEQ ID NO:5:
```

```
    (i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:5:

CAGCGGAACC GCTCATTGCC AATGG                                           25

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:6:

ATGCCCTCCC CCATGCCATC CTGCGT                                          26

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:7:

ATTGATGGTC TCTTTTAA                                                   18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:8:

ATGGGGGAGG GCATACCC                                                   18

(2) INFORMATION FOR SEQ ID NO:9:

(i) SEQUENCE CHARACTERISTICS:
        (A) LENGTH: 142 base pairs
        (B) TYPE: nucleic acid
        (C) STRANDEDNESS: single
        (D) TOPOLOGY: linear (ii) MOLECULE TYPE: synthetic DNA (HIV)

(xi) SEQUENCE DESCRIPTION: SEQ ID NO:9:

AGTGGGGGGA CATCAAGCAG CCATGCAAAT GTTAAAAGAG ACCATCAATG AGGAAGCTGC     60

AGAATGGGAT AGATTGCATC CAGTGCATGC AGGGCCTATT ACACCAGGCC AGATGAGAGA    120

ACCAAGGGGA AGTGACATAG CA                                            142

(2) INFORMATION FOR SEQ ID NO:10:

(i) SEQUENCE CHARACTERISTICS:
```

```
        (A)  LENGTH: 295 base pairs
        (B)  TYPE: nucleic acid
        (C)  STRANDEDNESS: double
        (D)  TOPOLOGY: linear (ii) MOLECULE TYPE: genomic DNA (a-actin)

(xi) SEQUENCE DESCRIPTION: SEQ ID NO:10:

TCACCCACAC  TGTGCCCATC  TACGAGGGGT  ATGCCCTCCC  CCATGCCATC  CTGCGTCTGG        60

ACCTGGCTGG  CCGGGACCTG  ACTGACTACC  TCATGAAGAT  CCTCACCGAG  CGCGGCTACA       120

GCTTCACCAC  CACGGCCGAG  CGGGAAATCG  TGCGTGACAT  TAAGGAGAAG  CTGTGCTACG       180

TCGCCCTGGA  CTTCGAGCAA  GAGATGGCCA  CGGCTGCTTC  CAGCTCCTCC  CTGGAGAAGA       240

GCTACGAGCT  GCCTGACGGC  CAGGTCATCA  CCATTGGCAA  TGAGCGGTTC  CGCTG           295
```

METHOD AND REAGENT FOR DETECTING MULTIPLE NUCLEIC ACID SEQUENCES IN A TEST SAMPLE

TECHNICAL FIELD

The present invention relates to detecting nucleic acid sequences and, in particular, relates to detecting a plurality of nucleic acid sequences in a test sample.

BACKGROUND OF THE INVENTION

Since the advent of the polymerase chain reaction (PCR), several variations to this nucleic acid amplification reaction have been devised. Additionally, several distinct nucleic acid amplification reactions have been introduced. For example, the ligase chain reaction (LCR) is an effective means for amplifying a nucleic acid sequence. Both PCR and LCR can be used to detect, for example, a pathogen in a test sample by amplifying a nucleic acid sequence unique to the particular pathogen (sometimes called a target sequence), then detecting the amplified nucleic acid sequences. The amplified nucleic acid sequences can be detected using techniques similar to those used in heterogeneous immunoassays.

A challenge facing the further development of amplification reactions includes detecting multiple target sequences in a test sample. Multiple target sequences can be detected to determine the presence of multiple pathogens that may be present in a test sample, or alternatively, multiple target sequences can be detected to quantify a target sequence present in a test sample. Unfortunately, methods for detecting multiple target sequences, for whatever purpose, is somewhat limited by the methods for detecting the signal generating groups that can be associated with the amplified sequences. In particular, in order to detect multiple target sequences, the sequences must be distinguished from one another. While such distinctions can be made by associating the sequences with different signal generating moieties, difficulties are presented when the signals from these moieties are detected. For example, when multiple fluorescent moieties are employed, each of the multiple moieties may have a distinct absorbtion and emission wavelength which can be employed to distinguish one sequence from another. But this detection scheme calls for a complex detection system that can excite and detect fluorophores at multiple wavelengths. Moreover, as the number of different fluorescent moieties to be detected increases, so does the complexity of the optical system employed to detect the moieties. Unfortunately, such systems are limited by the number of different sequences which can be detected because the complexity of the optical system increases in a cost prohibitive manner.

Alternatively, using multiple enzymatic signal generating moieties has been proposed to detect multiple target sequences, but such a detection scheme uses complex reagent systems to produce and inhibit signals generated by the enzymes. As a result, the predominant method for detecting multiple nucleic acid sequences is gel electrophoresis which distinguishes nucleic sequences based upon molecular weight. Gel electrophoresis, however, is a labor intensive, and therefore time consuming, method of detection which is not amenable to automation or standardization. Thus, there is a need for a nucleic acid detection system which is capable of detecting a plurality of target sequences in a practical manner.

SUMMARY OF THE INVENTION

The present invention provides a method of detecting a plurality of target sequences in a test sample comprising the steps of: a) contacting a hybridization platform with the test sample; b) hybridizing at least one target sequence, which may be present in the test sample, to the hybridization platform to thereby generate a change in signal at a site where the target sequence is hybridized; and c) detecting a change in signal at the hybridization site as an indication of the presence of the target sequence in the test sample. The hybridization platform comprises at least two capture probes immobilized to a support material in a defined pattern. The capture probes have distinct sequences, and each of the capture probes is labeled with at least one member of signal generating system that generates a change in signal in a target dependent manner. In its entirety, the signal generating system may comprise PORSCHA dyes, at least one intercalating dye, or quencher and reporter groups.

The present invention also provides a hybridization platform comprising at least two capture probes immobilized to a solid support material. The capture probes have distinct sequences and are labeled with at least one member of signal generating system, such as those mentioned above, which are capable of generating a change in signal in a target dependent manner. Additionally, the capture probes are immobilized to the solid support material in a defined pattern.

DETAILED DESCRIPTION OF THE INVENTION

The present invention provides practical methods and reagents for detecting a plurality of target sequences that may be present in a test sample by exploiting (i) the ability of at least two capture probes to produce distinct signals in the presence and absence of a target sequence and (ii) spatial separation between the capture probes. The distinct signal or change in signal produced by an individual capture probe in the presence and absence of its target sequence can be, for example, a complete lack of signal in the absence of the target sequence and a detectable signal in the presence of the target sequence. Alternatively, a signal produced in the absence of the target sequence may change in wavelength or intensity in the presence of the target sequence. The changes in signal from multiple capture probes can be distinguished from one another based upon the spatial separation of the probes. As a result, the present invention can detect multiple target sequences using a plurality of reporter groups having a common absorbtion and emission spectrum which thereby dispenses with the need for complex detection systems which can distinguish different signals, even though such reporter groups and detection systems could be used. Moreover, the reagents and methods provided herein permit the detection of multiple target sequences in a homogeneous-like manner which dispenses with excess handling of reagents and therefore provides an environment where contamination is minimized.

According to the present invention, multiple target sequences can be detected by contacting a test sample with a hybridization platform to thereby immobilize the target sequences to the hybridization platform. A "test sample", as used herein, means anything suspected of containing the target sequences. The test sample can be derived from any biological source, such as a pysiological fluid, including, blood, saliva, ocular lens fluid, cerebral spinal fluid, sweat, urine, milk, ascites fluid, mucous, synovial fluid, peritoneal fluid, amniotic fluid, cells, and the like, or fermentation broths, cell cultures, chemical reaction mixtures and the like. Forensic materials such as, for example clothing, may also contain a target sequence and therefore are also within the meaning of the term test sample. The test sample can be used (i) directly as obtained from the source or (ii) following a pre-treatment to modify the character of the sample. Thus, the test sample can be pre-treated prior to use by, for example, preparing plasma from blood, preparing liquids from solid materials, diluting viscous fluids, filtering liquids, distilling liquids, concentrating liquids, inactivating interfering components, adding reagents, and the like. Test samples also can be pretreated to digest, restrict or render double stranded nucleic acid sequences single stranded. Moreover, test samples may be pretreated to accumulate, purify, amplify or otherwise concentrate target sequences that may be contained therein. Amplification reactions that are well known in the art can be used to amplify target sequences. A "target sequence" as used herein means a nucleic acid sequence which is amplified, detected or both amplified and detected.

A "hybridization platform" as used herein means a solid support material that has a defined pattern of capture probes immobilized thereon. A "solid support material" refers to any material which is insoluble, or can be made insoluble by a subsequent reaction. The solid support can be chosen for its intrinsic ability to attract and immobilize a capture probe, or the solid support can retain an additional receptor which has the ability to attract and immobilize a capture probe. The additional receptor can include a charged substance that is oppositely charged with respect to a capture probe, or the receptor molecule can be any specific binding member which is immobilized upon (attached to) the solid support material and which has the ability to immobilize the capture probe through a specific binding reaction. The receptor molecule enables the indirect binding of a capture probe to a solid support material before the performance of the assay or during the performance of the assay. The solid support material thus can be, for example, latex, plastic, derivatized plastic, magnetic or non-magnetic metal, glass or silicon surface or surfaces of test tubes, microtiter wells, sheets, beads, microparticles, chips, and other configurations known to those of ordinary skill in the art. Such materials may be used in suitable shapes, such as films, sheets, or plates, or they may be coated onto or bonded or laminated to appropriate inert carriers, such as paper, glass, plastic films, or fabrics.

While microparticles, beads and similar solid support configurations can be employed according to the present invention, these support material configurations require segregation when coated with different capture probes so that the signals associated with a given capture probe can be distinguished from a signal associated with another capture probe attached to another, for example, microparticle. Such segregation techniques are well known in the art and may include fluid flow fractionation techniques which separate particulate matter based upon size. Hence, when particulate solid support materials are employed, particles having different sizes coated with distinct capture probes can be employed. Preferably, however, planar support materials such as, for example, glass chips are employed because of the ease with which a defined pattern of oligonucleotides can be immobilized to such a surface.

The term "capture probes" encompasses oligonucleotides and polynucleotides complementary to selected target sequences. Capture probes may comprise, for example, nucleic acid, ribonucleic acid and nucleic acid analogs such as uncharged nucleic acid analogs including, but not limited to, peptide nucleic acids (PNAs) which are disclosed in International Patent Application WO 92/20702 or morpholino analogs which are described in U.S. Pat. Nos. 5,185,444, 5,034,506, and 5,142,047. Additionally, as it will become apparent based upon the discussion below, the capture probes may also comprise combinations of these nucleic acid materials.

The capture probes are labeled with a "signal generating system" which, as used herein, means a label or labels that generate differential signals in the presence and absence of target. Thus, a signal is generated in a "target dependent manner" which means that in the absence of target sequence, a given signal is emitted which undergoes a detectable change upon hybridization between a capture probe and its target sequence. Capture probes can be labeled such that they emit a signal in a target dependent manner by labeling a probe with a signal generating group (variably referred to in this embodiment as a "reporter group") and a quenching group such that the signal generated by the reporter group is suppressed by the quenching group in the absence of the target sequence. Such reporter/quencher pairs have previously been described in U.S. Pat. No. 5,487,972 and U.S. Pat. No. 5,210,015 and may include, for example fluorophores such as rhodamine, coumarin, and fluorescein and well as derivatives thereof such as Tamra® (6-carboxy-tetramethyl-rhodamine), Texas Red®, Lucifer Yellow, 7-hydroxy-coumarin, and 6-carboxy-fluorescein. Another example of a capture probe capable of generating a signal in a target dependent manner includes a probe labeled with a PORSCHA dye or an intercalating dye. PORSCHA dyes have been described in U.S. Pat. No. 5,332,659 and demonstrate a change in fluorescence based upon the proximity of one PORSCHA dye with another. Intercalating dyes have been described in PCT Application No. WO 95/01341, D. Figeys, et. al., Journal of Chromatography A, 669, pp. 205–216 (1994), and M. Ogur, et. al., BioTechniques 16(6) pp. 1032–1033 (1994); and demonstrate an increase in fluorescence intensity when associated with a double stranded nucleic acid sequence as opposed to the fluorescence intensity emitted by such a dye associated with a single stranded nucleic acid sequence.

Based upon the above discussion, those skilled in the art will recognize that the signal generating system can be broken down into component parts or "members of the signal generating system". For example, a quenching group is one member of a reporter/quenching group signal generating system. Alternatively, for example, a single PORSHA dye is one member of a PORSHA dye signal generating system.

The labeled capture probes, as well as primer sequences that can be employed according to the present invention, can be prepared by any suitable method. For example, chemical synthesis of oligonucleotides has previously been described in, for example, U.S. Pat. No. 4,458,066, U.S. Pat. No. 4,415,732 and U.S. Pat. No. 4,948,882.

Figure 1:
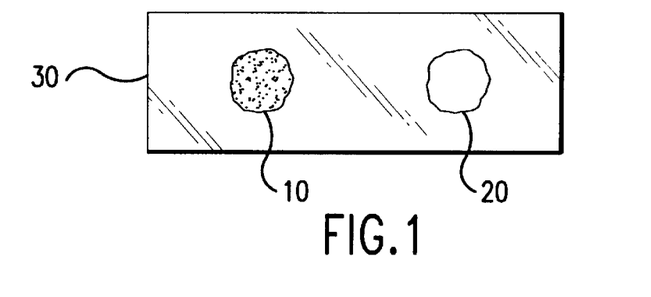
FIG. 1 is a schematic representation of a hybridization platform having a defined pattern of capture probes.

A "defined pattern" of capture probes immobilized to the solid support material means that the sequence of a capture probe immobilized at a particular site on the support material is known. The pattern may be as simple as at least two different oligonucleotides spotted on a planar support material such as that shown in FIG. 1 where spots 10 and 20 represent capture regions where capture probes having known sequences are immobilized on support material 30. More complex patterns, such as support materials having more than at least two sites having different capture probes immobilized thereon, can also be employed and have been described in U.S. Pat. No. 5,405,783, U.S. Pat. No. 5,412,087, Southern E. M., et. al., *Nucleic Acids Research*, Vol. 22, No. 8, pp. 1368–1373 (1994) and Maskos U., et. al., *Nucleic Acids Research*, Vol. 21, No. 20, pp. 4663–4669 (1993). In any case, the pattern is defined and therefore, the sequence of a capture probe or capture probes at a particular site on the support material is known.

Capture probes may be bound to a support material using any of the well known methodologies such as, for example, adsorption, covalent linkages, specific binding member interactions, or gold thiolate interactions. Capture probes also can be synthesized directly to the support material as described in U.S. Pat. No. 5,405,783, and U.S. Pat. No. 5,412,087.

After a test sample is contacted with the hybridization platform, the capture probes hybridize with their respective target sequences, if present, to thereby immobilize the target sequences to the hybridization platform. Upon hybridization with a target sequence, the signal generating groups associated with a capture probe produce a detectable change in signal. The change is generally dependent upon the signal generating system associated with the probe, and such a change may be detectable upon hybridization of the target sequence with the capture probe. Alternatively, hybridization between the capture probe and target sequence may trigger a cascade of events leading to the detectable change in signal.

For example, in the case where a capture probe is labeled with an intercalation dye, the fluorescent signal emitted from the dye increases in intensity upon hybridization between the capture probe and its complementary target sequence. Prior to hybridization, the capture probe has a signal of a given intensity and when the capture probe is hybridized with the target sequence, the signal has a different intensity. This change in intensity can be detected as an indication that the target sequence is hybridized to the capture probe and therefore present in the test sample.

Alternatively, in the event a capture probe is labeled with a PORSCHA dye, a complementary target sequence labeled with another PORSCHA dye will change the spectral properties of the PORSCHA dye on the capture probe upon hybridization. The target sequence can be labeled with a PORSCHA dye before or after hybridization between the capture probe and target sequence by contacting the target sequence with a conjugate comprising a specific binding member conjugated to a PORSCHA dye. Specific binding members are well known and may include, for example, antibodies and antigens, haptens and antibodies, biotin and avidin, complementary nucleic acid sequences and the like. Alternatively, the target sequence can be amplified using an amplification primer labeled with a PORSCHA dye. Any of these methods can be employed to label a target sequence with a PORSCHA dye. Upon hybridization between a POR-SCHA labeled target sequence and a PORSCHA labeled capture probe, the change in signal can be detected as an indication of the presence of the target sequence on the hybridization platform and therefore the presence of the target sequence in the test sample.

As mentioned above, the presence of the target sequence may cause a sequence of events resulting in a detectable change in signal. Such a sequence of events may include degradation of the capture probe in a target dependent fashion. As used herein, the phraseology "degraded in a target dependent fashion" or the like, when used to describe degradation of the capture probes means that the probes are not degraded in the absence of target but are degraded when the capture probes are hybridized to a target sequence.

For example, a capture probe that can be degraded in a target dependent fashion to produce a detectable change in signal may comprise an RNA sequence having a sequence of DNA attached at both the 5' and 3' ends. Such a capture probe can be labeled such that one DNA sequence is labeled with a reporter group and the other DNA sequence is labeled with a quenching group. The capture probe can be immobilized to the support material so that the DNA strand labeled with the reporter group is immobilized closest to the support material, and the quenching group is separated from the reporter group by the RNA sequence. Thus, in the absence of target, the probe is a single stranded nucleic acid sequence labeled with a reporter group whose signal is quenched by the quenching group. However, when a complementary target sequence is bound to the capture probe, the probe can be degraded in a target dependent manner. Specifically, the presence of the target presents a substrate that can be degraded such that the quenching group is separated from the reporter group. As a result, there is a detectable change in signal that can be detected at the site of the probe to indicate the presence of the target sequence in the test sample.

Figure 2A:
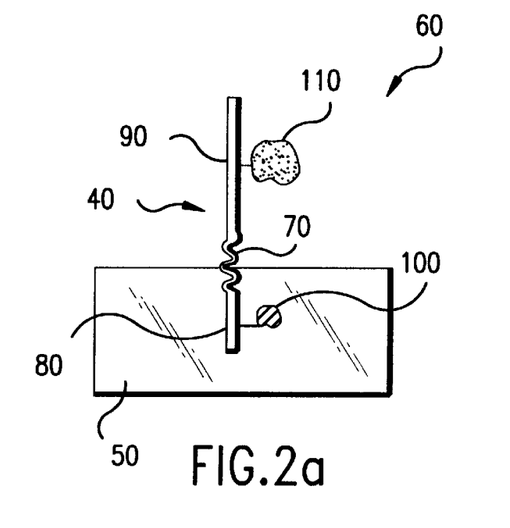
FIGS. 2a–2d illustrate an embodiment of the invention where a capture probe is degraded in a target dependent manner.
Figure 2B:
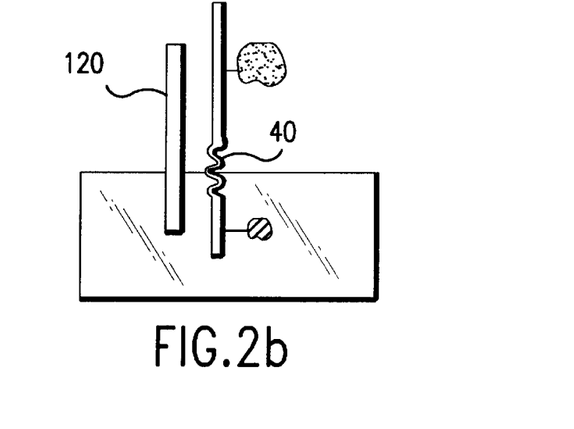
Figure 2C:
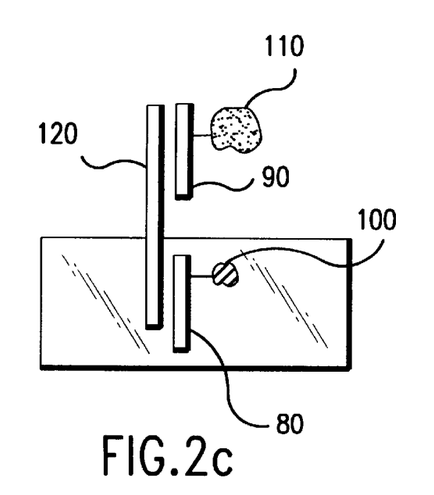
Figure 2D:
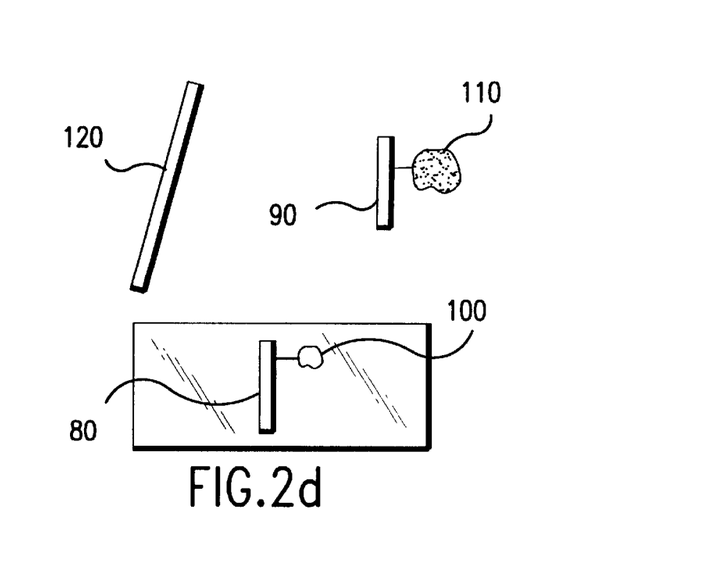

Several methods can be employed to degrade a labeled DNA/RNA/DNA capture probe in a target dependent manner. Specifically, when a target sequence is hybridized to such a capture probe, the double stranded sequence can be contacted with an enzyme having RNase H like activity which digests RNA in a DNA/RNA duplex and leaves the outer DNA portions of the capture probe hybridized to the target. With only the DNA portions remaining, the hybridization strength between the DNA portions of the capture probe and the target sequence is reduced. As a result, the target may spontaneously dissociate from the DNA portions, or an increase in stringency (eg. temperature) will dissociate the remaining portions of the probe from the target, to thereby separate the quenching group from the reporter group. A detectable change in signal is therefore provided that can be detected as an indication of the presence of the target sequence in the test sample. Target dependent degradation in this manner, is shown in FIGS. 2a–2d. FIG. 2a shows capture probe 40 immobilized to support material 50 to form hybridization platform 60. As shown by FIG. 2a, capture probe 40 comprises RNA sequence 70 (shown as a zig-zag line) and DNA sequences 80 and 90 attached at the 3' and 5' ends of RNA sequence 70. Also shown in FIG. 2a is the reporter group 100 and quenching group 110. FIG. 2b shows the hybridization platform after a target sequence, 120, is hybridized to capture probe 40. Hybridization platform 60 and immobilized target sequence 120 can then be contacted with RNase H which degrades the RNA sequence of capture probe 40, which as shown in FIG. 2c, leaves DNA sequences 80 and 90 attached to the target sequence. FIG. 2d, shows separation of quenching group 110 from reporter group 100 which remains bound to the solid support thereby allowing detection of the signal from the reporter group at the site of the capture probe.

While RNase H has been exemplified as a means for degrading a DNA/RNA/DNA capture probe, several other enzymes and probe designs could achieve the same effect. For example, using a similar type of capture probe, but containing an abasic site rather than RNA, enzymes having endonuclease IV activity could be employed to degrade the abasic portion of the capture probe to release the quenching group from the reporter group and produce a detectable change in signal. Alternatively, enzymes having exonuclease III activity could be used with a DNA capture probe which, after hybridization of the probe and target sequence, would degrade the probe in a 3' to 5' direction to thereby release the quencher group from the reporter group and produce a detectable change in signal. As a further alternative, the probe may comprise the DNA/RNA/DNA configuration, or DNA exclusively, and selected such that upon hybridization with the target sequence, a restriction site is presented. Hence, upon hybridization a restriction enzyme could be employed to sever the double stranded capture probe-target sequence complex and therefore separate the quenching group from the reporter group. Restriction enzymes such as BamH I or II, PST I, Ecor I, HincII, Taq I, as well as the restriction sites upon which they act, are well known in the art and are examples of enzymes that can be employed according to the present invention.

Alternatively a DNA capture probe can be degraded in a target dependent manner to permit a detectable change in signal according to an amplification reaction/primer extension based degradation. According to this embodiment, an amplification primer is employed in conjunction with the target sequence to degrade the capture probe and thereby separate the quenching group from the reporter group. According to this embodiment, both the capture probe and amplification primer hybridize to the target sequence such that the primer and probe are adjacent to one another. As used herein, the term "adjacent" when used to describe the relationship between the primer and probe on the target sequence, shall mean that the primer and probe are complementary to different portions of the same strand of the target sequence and therefore, do not overlap when hybridized to the target sequence. Additionally, the probe will be adjacent to the 3' end of the primer sequence so that the probe sequence lies in the path of primer extension. In the presence of reagents necessary for primer extension, such as for example, an enzyme having polymnerase and nuclease or exonuclease activity, and a supply of nucleotide triphosphates, primer extension will result in degradation of the probe by the nuclease or exonuclease activity of the enzyme extending the primer. Enzymes with polymerase as well as nuclease or exonuclease activity are well known and include, for example, E. coli DNA polymerase I or Taq polymerase. Hence, as the primer is extended, the probe will be degraded thereby separating the quenching group from the reporter group and permitting a detectable change in signal. In addition, in the absence of target sequence, the probe will not hybridize with the target, the primer will not prime target extension and the probe will not be degraded.

As noted above, an advantage of the present invention is the ability to detect multiple target sequences at a common absorption and emission spectrum because of the spatial separation between reporter groups affixed to the support material. Hence, with respect to certain embodiments where a probe is degraded in a target dependent manner using nuclease or exonuclease activity, the connection between the reporter group and the support material remains intact.

Figure 3A:
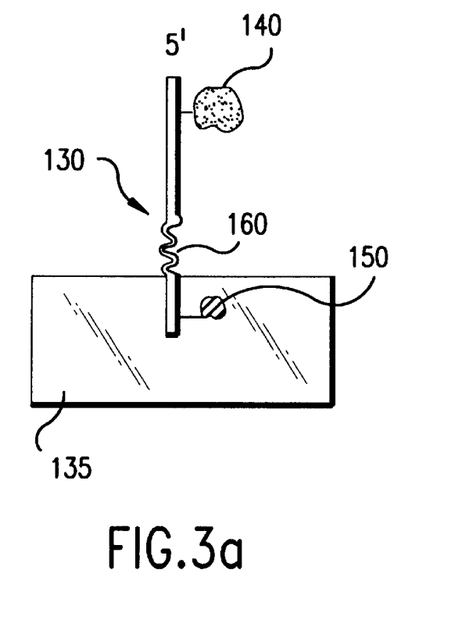
FIGS. 3a–3c are schematic representations of capture probes that can be employed according to the present invention.

Several methods can be employed for maintaining the connection between the reporter group and the support material. Several capture probe designs can be employed for stopping degradation of the capture probe and will be described in combination with FIGS. 3a–3c. For example, in the 3' direction from the reporter group, the probe may comprise nucleic acid analogs, which are not susceptible to nuclease or exonuclease activities. As shown in FIG. 3a, capture probe 130, shown immobilized to support material 135, comprises quenching group 140 and reporter group 150 which is between quenching group 140 and support material 135. Between quenching group 140 and reporter group 150, are one or more nucleotide analogs 160 designated as a (zig-zag line) lines.

Figure 3B:
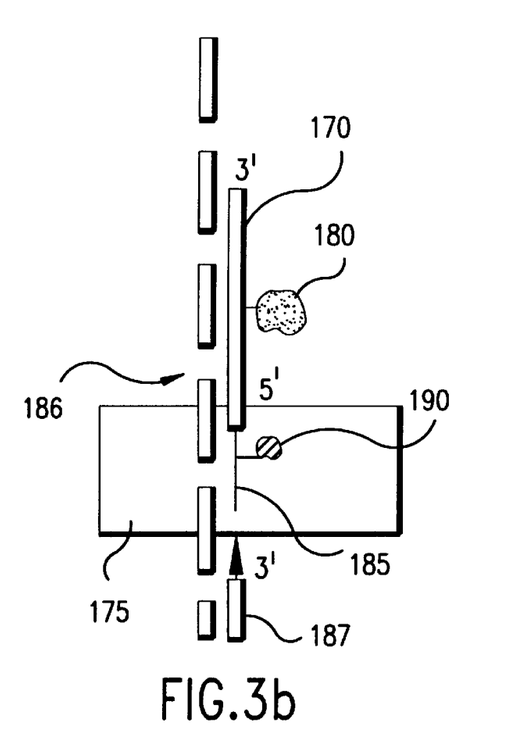

Alternatively, the capture probe can hybridize with the target sequence such that, when hybridized to the target sequence, the 5' end of the capture probe is adjacent to the 3' end of an amplification primer. This configuration is shown in FIG. 3b where capture probe 170, shown immobilized to support material 175, comprises quenching group 180 at the 3' end of probe 170, and reporter group 190 immobilized between the quenching group 180 and support material 175. According to this embodiment, it is preferable to use a linking group to attach the probe to the support material and attach the reporter group to the linker. As shown in FIG. 3b, linking group 185 is employed to attach capture probe 170 to support material 175. Also shown in FIG. 3b, reporter group 190 is attached to linking group 185. Further, FIG. 3b shows target sequence 186 hybridized to capture probe 170, and primer 187 hybridized to target sequence 186 such that the 3' end of the primer is adjacent to the 5' end of the capture probe. Upon extension of primer 187, probe 170 is degraded to release quenching group 180. However, the linkage between support material 175 and reporter group 190 remains undegraded.

Figure 3C:
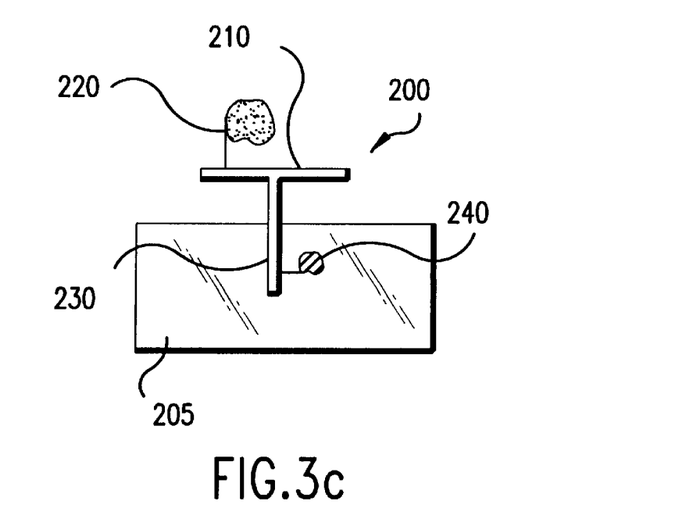

As a further alternative, the probe can be branched with the quenching group attached to a branch which is complementary to the target sequence and not directly attached to the solid support; and the reporter group is attached to a branch directly attached to the solid support and not typically complementary to the target. This probe configuration is shown in FIG. 3c where capture probe 200 comprises cross member 210 having a quenching group 220 immobilized thereon. Cross member 210 is attached to upright member 230 which has a reporter group 240 immobilized thereon. Capture probe 200 is attached to support material 205 via upright member 230. While upright member 230 is generally not complementary to the target sequence, cross member 210 is complementary to the target sequence and upon extension of a primer complementary to the target sequence, cross member 210 is degraded but upright member 230 is not. Consequently, quenching group 220 is released from capture probe 200 and reporter group 240 remains at its defined position. As a result a signal can be detected at this site to indicate the presence of a target sequence in the sample. Such branched probes can be synthesized using asymmetric branched phosphoramidites commercially available from Clontech, Palo Alto, Calif. Alternatively, the branch which is complementary to target sequence can be connected to the solid support using a non-nucleotide spacer such as polyoxyethylene spacers.

As a further alternative, the portion of a capture probe comprising the reporter group can be immobilized to the support material with a non-nucleotide chemical linking group which is not susceptible to degradation by exonucleolytic enzyme activity. Additionally, the sequence between the quencher and reporter group can be sufficiently long so that the reporter group is not degraded from the support material. Preferably, such an intervening sequence between the reporter and quenching group is greater than about 25 nucleotides long, and preferably more than about 30 nucleotides long.

According to embodiments where the capture probe is degraded in a target dependent manner, the portion of the capture probe that is labeled with the quenching group is susceptible to degradation and upon degradation, the quenching group is released from the reporter group. However, the portion of the capture probe, or linking group, labeled with the reporter group is permanently immobilized to the support material. As used herein, the terminology "permanently immobilized" when used to describe the linkage between the support material and the reporter group means that the reporter group will not be degraded from, or otherwise detached from, the support material prior to detecting a signal from the reporter group. Hence, when the capture probes are degraded and the quenching group is separated from the reporter group, the reporter group nevertheless remains immobilized to the support material at its defined position. A signal can therefore be detected at the site of the capture probe to indicate the presence of the target sequence in the test sample.

Amplification reactions which can be employed as a test sample pre-treatment or to degrade a capture probe in a target dependent manner are well known and can include the polymerase chain reaction (PCR) which has been described in U.S. Pat. Nos. 4,683,195 and 4,683,202, the ligase chain reaction (LCR) described in EP-A-320 308, gap LCR (GLCR) described in European Patent Application EP-A-439 182, or multiplex LCR described in International Patent Application No. WO 93/20227. "3SR" (Self-Sustained Sequence Replication) described in Fahy, E., et. al., *PCR Methods and Applications*, 1: 25–33 (1991) and "SDA" (Strand Displacement Amplification) described in Walker, G.T., et. al., *PNAS* 89: 392–396 (1992), as well as amplification reactions disclosed in U.S. Pat. No. 5,487,972 and 5,210,015 may also be employed according to the present invention.

The signal emitted by the various signal generating groups at the various locations on the hybridization platform can be detected at multiple wavelengths but it is preferable to detect the various signals at single wavelength because a more practical detection system can be employed to detect multiple target sequences. The method for detecting the signals is largely a matter of choice for one skilled in the art based upon signal emitted by the signal generating group employed. In any event, signals are collected from the various capture sites on the hybridization platform, and based upon the location of the signals, the presence of multiple target sequences in the test sample can be determined because of the capture probes' arrangement in a defined pattern.

According to the methods for detecting a target sequence provided herein, a test sample suspected of containing the target sequence is contacted with the hybridization support. The test sample may or may not be pretreated as mentioned above, but in either case the target sequence is denatured typically by heating the test sample to a temperature between about 80° C. and about 105° C. for times ranging from a few seconds to minutes in duration. Upon cooling, the target sequences, if any, are then able to hybridize to the capture probes present at defined areas on the solid support material. Hybridization of the target to the capture probes triggers a signal or triggers events which create a signal and therefore a signal at the various defined capture regions is referred to as being created in a "target-dependent manner".

According to one embodiment, a test sample can be pre-treated to amplify any target sequences contained therein. The amplification primers employed can be labeled with a PORSCHA dye so that any amplified target sequences are labeled with a PORSCHA dye. The labeled target sequences, if any, are then contacted with a hybridization platform comprising at least two capture probes, each of which is complementary to a different target sequence, immobilized to a support material at defined sites. The capture probes are also labeled with a PORSCHA dye. Upon hybridization of a target sequence with a capture probe, the spectral properties of the PORSCHA dye associated with the capture probe change, and this change can be detected as an indication of the presence of the target sequence in the test sample. If a particular capture probe's target sequence were not present, the spectral properties of the PORSCHA dye associated with the capture probe would remain the same, indicating the absence of the particular target sequence.

In another embodiment, a test sample can be pre-treated to amplify any target sequences contained therein. Any amplified target sequences can then be contacted with a hybridization support comprising a pattern of capture probes complementary to the various target sequences. Additionally, the capture probes may comprise intercalation dyes. Alternatively, target sequences may be labeled with the intercalation dye, via the amplification reaction, and the probe may be free of an intercalation dye. Upon hybridization with the target sequences, the dyes on the capture probes, or target sequences, intercalate between the double stranded sequences and demonstrate an increase in fluorescence. Accordingly, in the presence of an individual capture probe's target sequence, a detectable change in signal will be detected at the site of that capture probe. Hence, a change in signal at any or all of the capture probe sites can be detected to indicate the presence of any or all of the target sequences in a test sample.

According to still another embodiment, a test sample can be pretreated to amplify any target sequences contained therein and contacted with a hybridization platform. The platform may comprise a defined pattern of capture probes immobilized to a support material and the probes may comprise a nucleic acid or combination of nucleic acids having an end immobilized to the support material. The probe may be labeled with a quenching and reporter group such that the reporter dye is closest to the end of the probe that is immobilized to the support material and therefore between the support material and the quenching group. After contacting the hybridization platform with the test sample, any target sequences contained therein will hybridize to the various capture probes. The probes can then be degraded by contacting the capture support and any target sequences immobilized thereon with, for example, a restriction enzyme or RNase H to thereby release the quenching group from the support material. Upon release of the quenching group, the signal from the reporter group can be detected as an indication of the presence of the target sequence in the test sample. Detecting signals at the defined capture probe sites can therefore be used as an indication of the target sequences in the test sample.

Still another embodiment of the invention comprises a method whereby a test sample, and any target sequences therein, is contacted with a hybridization platform. Additionally, the hybridization platform can be contacted with reagents for performing an amplification reaction. The hybridization platform may comprise at least two capture probes immobilized to a support material and the capture probes may be labeled with a reporter and a quenching group such that the reporter group is between the support material and the quenching group. Between the quenching group and reporter group, however, are means for stopping the degradative processes of, for example, an enzyme having exonuclease activity. After such a hybridization support is contacted with a test sample and amplification reagents, target sequences, if any, hybridize with the capture probes, and amplification primers hybridize with the target sequence. With the amplification primer hybridized to the target sequence, primer extension may occur in the direction of the capture probe which results in degradation of the probe up to the point where there are means for stopping degradation. Thus, primer extension releases the quenching group from the reporter group but will not remove the reporter group from the support material. Hence, in the absence of a target sequence, no signal will be detected from the site where the capture probe specific for that target sequence is located. On the other hand, in the presence of a particular target sequence, a signal will be detectable from the site where its complementary capture probe was immobilized. In this manner, a signal detected at a particular site on the hybridization platform indicates the presence of its complementary target sequence in the test sample. Accordingly, detecting signals at multiple defined capture probe sites is an indication of the presence of the target sequences in the test sample.

Figure 4A:
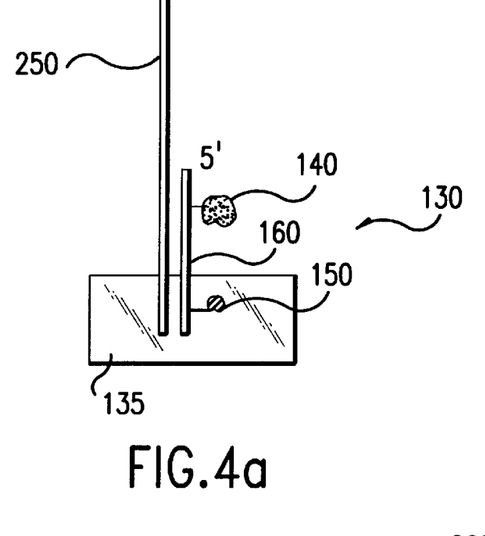
FIGS. 4a–4c schematically represent an embodiment of the invention where a signal is generated by a reporter group in a target dependent manner.
Figure 4B:
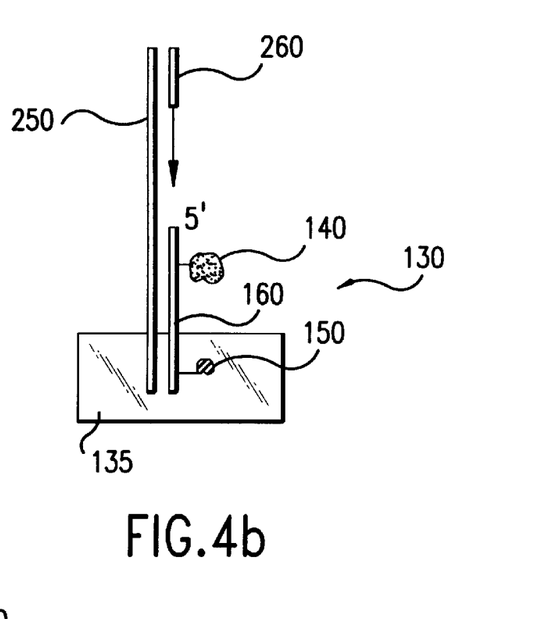
Figure 4C:
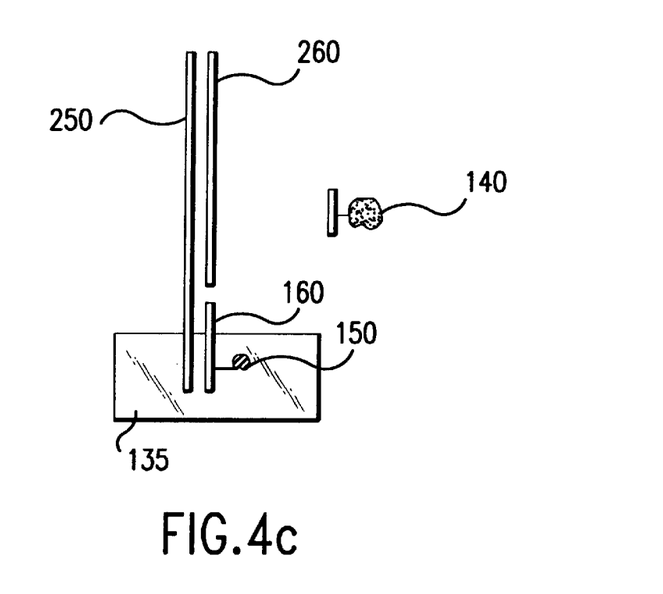

FIGS. 4a–c schematically represent the preceding embodiment at one site on a hybridization platform. FIG. 4a shows target sequence 250 hybridized to the hybridization platform described in FIG. 3a where capture probe 130 is immobilized to support material 135 and comprises reporter group 150, quenching group 140, and nucleic acid analogs 160. FIG. 4b shows the hybridization platform of 4a after the addition of amplification reagents including, for example, an enzyme having polymerase and exonuclease activity, an amplification primer and a supply of nucleotide triphosphates. As shown by the arrow in FIG. 4b, primer extension begins and proceeds in the direction of capture probe 130. FIG. 4c, shows the hybridization platform after primer extension has proceeded to the point where nucleic acid analogs 160 are located. As a result, quenching group 140 has been released from the capture probe and primer extension has stopped. Consequently, a signal from reporter group 150 can be detected as an indication of the presence of target sequence 250 in the test sample.

Advantageously, the design of the hybridization platform permits embodiments of the present invention to be performed in a homogeneous fashion. Accordingly, all reagents for performing the various embodiments can be contacted with the hybridization support all at once and a vessel containing the hybridization platform can be sealed to thereby avoid problems associated with contamination.

The following examples are provided to further illustrate the present invention and are not intended to limit the invention.

EXAMPLES

The following examples demonstrate use of the present invention for detecting DNA from HIV (SEQUENCE ID NO 9) and/or exon 3 of the human β-actin gene (SEQUENCE ID NO 10) using DNA oligomer primers and oligonucleotide capture probes attached to a solid phase. These primers and probes are identified as SEQUENCE ID NO 1, SEQUENCE ID NO 2, SEQUENCE ID NO 3, SEQUENCE ID NO 4, SEQUENCE ID NO 5, SEQUENCE ID NO 6, SEQUENCE ID NO 7 and SEQUENCE ID NO 8. SEQUENCE ID NO 1, 2, 3 and 7 are specific for HIV. SEQUENCE ID NO 4, 5, 6 and 8 are specific for actin. HIV specific primers are SEQUENCE ID NO 1 and SEQUENCE ID NO 2. The HIV specific capture probes are SEQUENCE ID NO 3 and SEQUENCE ID NO 7. Actin specific primers are SEQUENCE ID NO 4 and SEQUENCE ID NO 5 and the actin specific capture probes are SEQUENCE ID NO 6 and SEQUENCE ID NO 8.

Example 1

Preparation of Primers and Probes

A. Primer Sets

Target-specific primers are designed to hybridize with and prime extension of copies of either the HIV or actin target sequences. These primers are SEQUENCE ID NO 1 and SEQUENCE ID NO 2 for HIV and SEQUENCE ID NO 4 and SEQUENCE ID NO 5 for actin. Primer sequences are synthesized using standard oligonucleotide synthesis methodology.

For use with PORSCHA solid phase probes, SEQUENCE ID NO 1 for HIV and SEQUENCE ID NO 4 for actin is labeled at the 3' end with pyrene by using a pyrene nucleoside phosphoramidite (Kidwell, U.S. Pat. No. 5,332,659) as the second incorporated nucleotide used in oligo synthesis, followed by the remaining nucleotides shown in SEQ ID NOs. 1 and 4.

B. Extension Degraded Solid Phase Probes For 3' Solid Phase Immobilization

Capture probes are designed to hybridize with the HIV (SEQUENCE ID NO 3) target or actin target (SEQUENCE ID NO 6) and to have a Tm at least 5° C. higher than the Tm of the adjacent primer. The probe sequences are synthesized using standard oligonucleotide synthesis methodology. The 3' residue of the probes is a 3' thiol coupler (Genosys Biotechnologies, Inc., The Woodlands, TX), followed by a C12 polyethylene oxide linker spacer phosphoramidite (Clontech Laboratories, Inc., Palo Alto, Calif.). A fluorescein reporter group is added next using fluorescein-ON phosphoranridite (Clontech Laboratories, Inc., Palo Alto, Calif.), followed by SEQUENCE ID NO 3 for the HIV probe or SEQUENCE ID NO 6 for the actin probe. An amino functionality is added to the 5' end and the oligos are released from the solid phases used for synthesis. The active ester of the amino reactive quencher TAMRA-NHS (6-carboxy- tetramethyl-rhodamine n-hydroxy succinimide, Perkin-Elmer, Applied Biosystems Division, Foster City, Calif.) is then incorporated onto the 5' end of the probes by reaction with the terminal amino group.

Probes are then coupled to the solid phase through the 3' disulfide residue of the oligo. The solid phase consists of 0.005" Kapton sputtered with a thin (500 Å) layer of titanium followed by a 5200 Å layer of gold. Probes in 25 mM Tris, pH 8 at a concentration of $5 \times 10^{12}$ molecules/µl are applied to the gold in a volume of 0.2 µl ($1 \times 10^{12}$ molecules/spot) at a known separate location for each probe, and allowed to dry.

C. Extension Degraded Solid Phase Probes For 5' Solid Phase Immobilization

Capture probes are designed to hybridize with the HIV (SEQUENCE ID NO 3) target or actin target (SEQUENCE ID NO 6) and to have a Tm at least 5° C. higher than the Tm of the adjacent primer. The probe sequences are synthesized using standard oligonucleotide synthesis methodology. The 3' residue of the probes is a linker arm nucleotide (LAN) phosphoramidite (Glen Research, Sterling, Va.); a nucleotide with a 6-carbon linker arm attached to the base. SEQUENCE ID NO 3 for the HIV probe or SEQUENCE ID NO 6 for the actin probe follows the LAN phosphoranmidite. A fluorescein reporter group is added next using fluorescein-ON phosphoramidite (Clontech Laboratories, Inc., Palo Alto, Calif.), followed by a C12 polyethylene oxide linker spacer phosphoramidite (Clontech Laboratories, Inc., Palo Alto, Calif.). The 5' residue of the probes is a 5' thiol coupler (Genosys Biotechnologies, Inc., The Woodlands, Tex.). The oligos are released from the solid phases used for synthesis and the 3' ends are blocked with phosphate. TAMRA-NHS (6-carboxy-tetramethyl-rhodamine n-hydroxy succinimide) ester (Perkin-Elmer, Applied Biosystems Division, Foster City, Calif.) is then coupled to the LAN-containing oligonucleotides.

Probes are then coupled to the solid phase through the 5' disulfide residue of the oligo. The solid phase consists of 0.005" Kapton sputtered with a thin (500 Å) layer of titanium followed by a 5200 Å layer of gold. Probes in 25 mM Tris, pH 8 at a concentration of $5 \times 10^{12}$ molecules/μl are applied to the gold in a volume of 0.2 μl ($1 \times 10^{12}$ molecules/spot) at a known separate location for each probe, and allowed to dry.

D. DNA/RNA/DNA Solid Phase Probes

SEQUENCE ID NO 3 for HIV, and SEQUENCE ID NO 6 for actin, are employed as DNA/RNA/DNA capture probes designed to hybridize with HIV or actin target sequences. The probe sequences are synthesized using standard oligonucleotide synthesis methodology. The 3' residue of the probes is a 3' thiol coupler (Genosys Biotechnologies, Inc., The Woodlands, Tex.), followed by a C12 polyethylene oxide linker spacer phosphoramidite (Clontech Laboratories, Inc., Palo Alto, Calif.). A fluorescein reporter group is added next using fluorescein-ON phosphoramidite (Clontech Laboratories, Inc., Palo Alto, Calif.), followed by 13 deoxyribonucleotide phosphoramidites of SEQUENCE ID NO 3 for the HIV probe or SEQUENCE ID NO 6 for the actin probe. Four ribonucleotide phosphoramidites representing the respective specific sequences are then inserted, followed by the remaining deoxyribonucleotide phosphoramidites of SEQUENCE ID NO 3 for the HIV probe or SEQUENCE ID NO 6 for the actin probe. An amino functionality is added to the 5' end and the oligos are released from the solid phases used for synthesis. The active ester of the amino reactive quencher TAMRA-NHS (6-carboxy-tetramethyl-rhodamine n-hydroxy succinimide, Perkin-Elmer, Applied Biosystems Division, Foster City, Calif.) is then incorporated onto the 5' end of the probes by reaction with the terminal amino group.

Probes are then coupled to the solid phase through the 3' disulfide residue of the oligo. The solid phase consists of 0.005" Kapton sputtered with a thin (500 Å) layer of titanium followed by a 5200 Å layer of gold. Probes in 25 mM Tris, pH 8 at a concentration of $5 \times 10^{12}$ molecules/μl are applied to the gold in a volume of 0.2 μl ($1 \times 10^{12}$ molecules/spot) at a known separate location for each probe, and allowed to dry.

E. Intercalating Dye Solid Phase Probes

SEQUENCE ID NO 3 for HIV, and SEQUENCE ID NO 6 for actin, are used to synthesize capture probes for HIV or actin target sequences. The probe sequences are synthesized using standard H-phosphonate oligonucleotide synthesis methodology (reagents available from Applied Biosystems, Inc., Foster City, Calif.). The 3' residue of the probes is a 3' disulfide phosphoramidite (Clontech Laboratories, Inc., Palo Alto, Calif.), followed by a C12 polyethylene oxide linker spacer phosphoramidite (Clontech Laboratories, Inc., Palo Alto, Calif.). SEQUENCE ID NO 3 for the HIV probe or SEQUENCE ID NO 6 for the actin probe follows the spacer and, during the synthesis, every fifth H-phosphonate is oxidized in the presence of phenanthridine-triamine to link this intercalating dye to the phosphate residue. The oligos are then released from the solid phase used for synthesis.

Probes are then coupled to the solid phase through the 3' disulfide residue of the oligo. The solid phase consists of 0.005" Kapton sputtered with a thin (500 Å) layer of titanium followed by a 5200 Å layer of gold. Probes in 25 mM Tris, pH 8 at a concentration of $5 \times 10^{12}$ molecules/μl are applied to the gold in a volume of 0.2 μl ($1 \times 10^{12}$ molecules/spot) at a known separate location for each probe, and allowed to dry.

F. PORSCHA Solid Phase Probes

SEQUENCE ID NO 7 for HIV, and SEQUENCE ID NO 8 for actin, are used to synthesize capture probes that hybridize with HIV or actin target sequences. The probe sequences are synthesized using standard oligonucleotide synthesis methodology. The 3' residue of the probes is pyrene nucleoside phosphoramidite (Kidwell, U.S. Pat. No. 5,332,659) which is the first incorporated nucleotide used in oligo synthesis, followed by SEQUENCE ID NO 7 for the HIV probe or SEQUENCE ID NO 8 for the actin probe. A C12 polyethylene oxide linker spacer phosphoramidite (Clontech Laboratories, Inc., Palo Alto, Calif.) follows the specific sequences. The 5' residue of the probes is a 5' thiol coupler (Genosys Biotechnologies, Inc., The Woodlands, Tex.). The oligos are then released from the solid phases used for synthesis.

Probes are then coupled to the solid phase through the 5' disulfide residue of the oligo. The solid phase consists of 0.005" Kapton sputtered with a thin (500 Å) layer of titanium followed by a 5200 Å layer of gold. Probes in 25 mM Tris, pH 8 at a concentration of $5 \times 10^{12}$ molecules/μl are applied to the gold in a volume of 0.2 μl ($1 \times 10^{12}$ molecules/spot) at a known separate location for each probe, and allowed to dry.

Example 2

Multiplex Amplification and Detection Using Extension Degraded 3' Solid Phase Probes Mixtures containing known amounts of DNA from HIV (cloned DNA devoid of β-actin gene DNA) and/or exon 3 of the human β-actin gene are PCR amplified and detected using primers described in Example 1.A. and solid phase probes described in Example 1.B. as follows: The primers are used at a concentration of 0.5 μM each. Taq polymerase is used at a concentration of 2.5 units per reaction. PCR is performed using 10× PCR buffer which consists of 500 mM KCl, 100 mM Tris-HCl, 15 mM $MgCl_2$, 0.01% (w/v) gelatin, pH 8.3, at a final concentration of 1×. The final concentration of $MgCl_2$ is 1.5 mM, with dNTP's used at 200 nM each, and 50 μg/ml BSA, in a total reaction volume of 0.2 ml.

190 μl of the above PCR mixture and 10 μl of target DNA are added to tubes containing HIV and actin capture probes attached to the gold solid phase as described in Example 1.B. The reaction mixture is amplified in a Perkin-Elmer 480 Thermal Cycler with a thermal profile of 95° C. for 1 minute, followed by 50 cycles of 95° C. for 60 seconds/60° C. for 80 seconds. This is followed by 95° C. for 5 minutes, then 15° C. for 30 minutes.

Reactivity of each spot on the gold solid phase is determined following PCR by monitoring the increase in reporter fluorescence at 518 nm, as well as fluorescence of the quencher group at 582 nm, following excitation at 488 nm using a surface fluorescence reader. The increase in fluorescence is compared to the fluorescence of a negative control (containing no target DNA). The reporter fluorescence (R) is divided by the quencher fluorescence (Q) giving an RQ ratio for each spot containing a probe on the gold solid phase. The difference between the sample RQ ratio and the negative control RQ ratio, known as delta RQ, represents the specific product amplification and detection (Livak, et al, PCR Methods and Applications 4: 357–362, 1995).

Samples containing HIV only show reactivity (increased fluorescence at 518 nm and increased delta RQ) at the spot where the HIV probe is attached but not at the spot where the actin probe is attached to the gold solid phase. Samples containing actin DNA only show reactivity at the spot where the actin probe is attached but not at the spot where the HJV probe is attached to the gold solid phase. Samples containing both HIV and actin show reactivity where both probes are attached, and samples containing neither HIV nor actin show no reactivity with the probes attached to the solid phase.

Example 3

Multiplex Amplification and Detection Extension Degraded 5' Solid Phase Probes

Mixtures containing known amounts of DNA from HIV and/or exon 3 of the human β-actin gene are PCR amplified and detected using primers described in Example 1.A. and solid phase probes described in Example 1.C. by the method described above in Example 2.

Reactivity and results are the same as described in Example 2.

Example 4

Multiplex Detection Using DNA/RNA/DNA Solid Phase Probes

Mixtures containing known amounts of DNA from HIV and/or exon 3 of the human β-actin gene are detected using solid phase probes described in Example 1.D., 10 μl of target DNA is added to tubes containing HWV and actin DNA/RNA/DNA probes attached to the gold solid phase as described in Example 1.D., 17 μl of 10× RNAse H buffer, 1–10 units of RNase H and molecular biology grade water to a volume of 170 μl. Tubes are incubated at 65° C. for 10 minutes, followed by 37° C. for 30 minutes.

Reactivity of each spot on the gold solid phase is determined after target detection by monitoring the increase in reporter fluorescence at 518 nm, as well as fluorescence of the quencher group at 582 nm, following excitation at 488 nm using a surface fluorescence reader. The increase in fluorescence is compared to the fluorescence of a negative control (containing no target DNA). The reporter fluorescence (R) is divided by the quencher fluorescence (Q) giving an RQ ratio for each spot containing a probe on the gold solid phase. The difference between the sample RQ ratio and the negative control RQ ratio, known as delta RQ, represents the specific target detection (Livak, et al, PCR Methods and Applications 4: 357–362, 1995).

Results are the same as described in Example 2.

Example 5

Multiplex Amplification and Detection Using Intercalating Dye Solid Phase Probes Mixtures containing known amounts of DNA from HIV (cloned DNA devoid of β-actin gene DNA) and/or exon 3 of the human β-actin gene are PCR amplified and detected using primers described in Example 1.A. and solid phase probes described in Example 1.E. as follows: The primers are used at a concentration of 0.5 μM each. Stoeffel fragment (Perkin-Elmer, Roche Molecular Systems, Inc., Branchburg, N.J.) is used at a concentration of 2.5 units. PCR is performed using 10× PCR buffer which consists of 500 mM KCl, 100 mM Tris-HCl, 15 mM $MgCl_2$, 0.01% (w/v) gelatin, pH 8.3, at a final concentration of 1×. The final concentration of $MgCl_2$ is 1.5 mM, with dNTP's used at 200 nM each, and 50 μg/ml BSA, in a total reaction volume of 0.2 ml.

190 μl of the above PCR mixture and 10 μl of target DNA are added to tubes containing HIV and actin probes attached to the gold solid phase as described in Example 1.F. The reaction mixture is amplified in a Perkin-Elmer 480 Thermal Cycler with a thermal profile of 95° C. for 1 minute, followed by 50 cycles of 95° C. for 60 seconds/60° C. for 80 seconds. This is followed by 95° C. for 5 minutes, then 15° C. for 30 minutes.

Reactivity on the gold solid phase is determined following PCR by monitoring the increase in fluorescence emission at 590 nm following excitation at 360 nm using a surface fluorescence reader. Emission of fluorescence at 590 nm results due to changes in the fluorescent properties of the dye upon intercalating into the double-stranded oligonucleotides formed by specific hybridization between probe and amplified target.

Samples containing HIV only show reactivity (increased emission at 590 nm versus negative control) at the spot where the HIV probe is attached but not at the spot where the actin probe is attached to the gold solid phase. Samples containing actin only show reactivity at the spot where the actin probe is attached but not at the spot where the HIV probe is attached to the gold solid phase. Samples containing both HIV and actin show reactivity where both probes are attached, and samples containing neither HIV nor actin show no reactivity with the probes attached to the solid phase.

Example 6

Multiplex Amplification and Detection Using PORSCHA Solid Phase Probes.

Mixtures containing known amounts of DNA from HIV (cloned DNA devoid of β-actin gene DNA) and/or exon 3 of the human β-actin gene are PCR amplified and detected using PORSCHA pyrene-labeled primers of SEQUENCE ID NO 1 and SEQUENCE ID NO 4 and unlabeled primers of SEQUENCE ID NO 2 and SEQUENCE ID NO 5 described in Example 1.A., and solid phase probes described in Example 1.F., by the procedure described above in Example 5.

Reactivity on the gold solid phase is determined following PCR using a surface fluorescence reader to monitor the increase in emitted light at 480 nm, following excitation at 343 nm, resulting from the overlap of the pi systems of the pyrene rings on the primer and probe when brought into proximity by specific hybridization. Emission at 378 and 396 nm is also monitored and represents the light emitted by the pyrenes on the primer and probe when they are too far apart to interact. The ratio of light emitted at 480 nm to emission at 378 and 396 nm represents the specific product amplification and detection.

Samples containing HIV only show reactivity (increased emission at 480 nm and increased 480: 378, 396 nm ratio) at the spot where the HIV probe is attached but not at the spot where the actin probe is attached to the gold solid phase.

Samples containing actin only show reactivity at the spot where the actin probe is attached but not at the spot where the HIV probe is attached to the gold solid phase. Samples containing both HIV and actin show reactivity where both probes are attached, and samples containing neither FHV nor actin show no reactivity with the probes attached to the solid phase.

While the invention has been described in detail and with reference to specific embodiments, it will be apparent to one skilled in the art that various changes and modifications may be made to such embodiments without departing from the spirit and scope of the invention. Additionally, all references and patents, including U.S. Patents or Foreign Patents, cited herein are hereby incorporated by reference.

What is claimed is:

1. A method of detecting a plurality of target sequences in a test sample comprising the steps of:
   a) amplifying said target sequences in said test sample to form amplified target sequences;
   b) contacting a hybridization platform with said amplified target sequences wherein
      (i) said hybridization platform comprises at least two capture probes immobilized to a support material in a defined pattern,
      (ii) said at least two capture probes have distinct sequences, and
      (iii) each of said capture probes is labeled with at least one member of a signal generating system wherein said signal generating system generates a change in signal in a target dependent manner;
   b) hybridizing at least two amplified target sequences to said hybridization platform to generate a change in signal at a site where said target sequence is hybridized; and
   c) detecting a change in signal at said site as an indication of the presence of said target sequence in said test sample.

2. The method of claim 1 wherein said capture probes are labeled with an intercalation dye and said change in signal is detected upon hybridization of said target sequences to said hybridization platform.

3. The method of claim 1 wherein said probes are labeled with a dye that changes its fluorescence characteristics when in proximity of another dye and said method further comprises the step of labeling said target sequences with a dye that changes its fluorescence characteristics when in proximity of another dye before or after hybridizing said at least two target sequences to said hybridization platform but before detecting said change in signal.

4. The method of claim 1 wherein said capture probes are labeled with a quenching group and a reporter group whereby said signal generating group is permanently immobilized to said support material and said method further comprises degrading said capture probes in a target dependent manner after hybridizing said target to said platform but before detecting said change in signal.

5. The method of claim 4 wherein degrading said capture probes comprises contacting said probes with an enzyme having an activity selected from the group consisting of: RNase H activity, restriction activity, endonuclease IV activity, endonuclease activity and exonuclease III activity.

6. A method of detecting a plurality of target sequences in a test sample comprising the steps of:

a) contacting a hybridization platform with said test sample comprising at least two target sequences wherein
   (i) said hybridization platform comprises at least two capture probes immobilized to a support material in a defined pattern,
   (ii) said at least two capture probes have distinct sequences, and
   (iii) each of said capture probes is labeled with a quenching group and a reporter group whereby the signal generating group is permanently immobilized to said support material;
b) hybridizing at least two target sequences to said hybridization platform and degrading said capture probes in a target dependent manner to generate a change in signal at a site where said target sequence is hybridized; and
c) detecting a change in signal at said site as an indication of the presence of said target sequence in said test sample.

7. The method of claim 6 wherein said reagents for performing an amplification reaction comprise:
   a) an enzyme having nuclease or exonuclease activity and polymerase activity; and
   b) nucleotide triphosphates.

8. The method of claim 7 wherein said capture probes further comprise means for stopping the degradation of said capture probes.

9. A kit comprising reagents for performing an amplification reaction and a hybridization platform comprising at least two capture probes immobilized to a solid support material wherein
   a) said capture probes have distinct sequences,
   b) each of said capture probes is labeled with at least one member of a signal generating system wherein said signal generating system generates a change in signal in a target dependent manner, and
   c) said capture probes are immobilized to said solid support material in a defined pattern.

10. The kit platform of claim 9 wherein said capture probes are labeled with a reporter group and a quenching group such that said signal generating group is permanently immobilized to said solid support material.

11. The kit platform of claim 10 wherein said capture probes comprise means for stopping capture probe degradation between said reporter group and said solid phase.

* * * * *

UNITED STATES PATENT AND TRADEMARK OFFICE
CERTIFICATE OF CORRECTION

PATENT NO. : 5,955,268
DATED : September 21, 1999
INVENTOR(S) : Edward N. Granados et al.

It is certified that error appears in the above-identified patent and that said Letters Patent is hereby corrected as shown below:

Column 22,
Line 59, replace "The kit platform of claim 9" with -- The kit of claim 9 --.
Line 63, replace "The kit platform of claim 10" with -- The kit of claim 10 --.

Signed and Sealed this

Eleventh Day of December, 2001

*Attest:*

*Attesting Officer*

NICHOLAS P. GODICI
*Acting Director of the United States Patent and Trademark Office*